United States Patent [19]

Abraham et al.

[11] Patent Number: 4,965,126
[45] Date of Patent: Oct. 23, 1990

[54] INK-REINFORCED POLYURETHANE FILMS

[76] Inventors: William W. Abraham, 37 Woodberry Rd., New Hartford, N.Y. 13413; John S. Gentelia, 274 Center Rd., Madison, N.Y. 13402

[21] Appl. No.: 349,488

[22] Filed: May 9, 1989

Related U.S. Application Data

[63] Continuation of Ser. No. 48,932, May 12, 1987.

[51] Int. Cl.$^5$ ............................................... C09U 7/02
[52] U.S. Cl. .................................. 428/343; 428/423.3; 428/195; 128/156
[58] Field of Search .................... 428/423.3, 343, 195; 128/156

[56] References Cited

U.S. PATENT DOCUMENTS

Re. 31,887  5/1985  Hodgson ............................ 428/343
4,156,067  5/1979  Gould .................................. 424/63

Primary Examiner—Edith Buffalow

[57] ABSTRACT

A reinforcement for thin film materials is provided by coating the films with an ink-type material. Ink coating of moisture vapor-permeable films such as polyurethane allows for a film suitable for use on skin which has an optimal rate of moisture vapor transmission. If desired, an adhesive can be provided on the ink-coated polyurethane membrane, and such materials are suitable for retaining I.V. needles and the like in place on a patient.

13 Claims, 1 Drawing Sheet

INK-REINFORCED POLYURETHANE FILMS

This is a continuation of application Ser. No. 048,932 filed May 12, 1987 now abandoned.

FIELD OF THE INVENTION

The present invention relates to ink-coated thin films and more specifically polyurethane films which are useful in holding I.V. needles in place.

BACKGROUND OF THE INVENTION

Adhesive materials provided for use on patients, such as for retaining I.V. needles in place, must provide protection against infection, while at the same time allowing epidermal water to evaporate. The material used must therefore allow a rate of moisture vapor transmission which is neither too low nor too high. Previous attempts at such adhesives, such as U.S. Pat. No. Re. 31,887, have provided a continuous backing material of unreinforced polyurethane film combined with a continuous adhesive. Such membranes often allow too much moisture to pass through, are much more likely to break apart, and are more difficult to apply than reinforced materials. It is therefore desirable to obtain a reinforced polyurethane backing material which maintains an optimal rate of moisture vapor transmission and provides more body for ease of application. It is also desirable to obtain other thin films which also have superior strength and tear resistance.

SUMMARY OF THE INVENTION

It has been discovered that coating portions of polyurethane or other films with ink provides a product of greater stability and applicability with a moisture vapor transmission rate lower than that of the bare membrane. An ink-coated polyurethane membrane, combined with a suitable adhesive, provides a stronger product which still maintains a sufficient level of moisture transmissability, and is thus a highly desirable material for retaining I.V. needles and the like on the skin.

The ink-coated polyurethane or other membranes of the present invention can also be used in applications not requiring an adhesive. For example, it may be more desirable to wrap an arm or other region with sheets of a non-adhesive thin film material. This film can be reinforced using the method of the present invention yet will not require an adhesive backing.

DETAILED DESCRIPTION OF THE PREFERRED EMBODIMENTS

Figure 1:
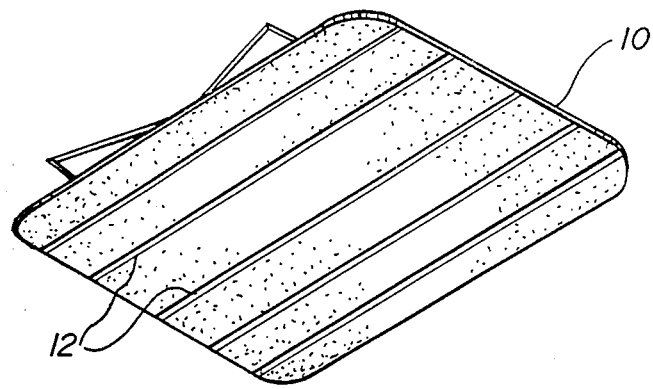
FIG. 1 is a perspective view of the reinforced polyurethane membrane of the present invention.
Figure 2:
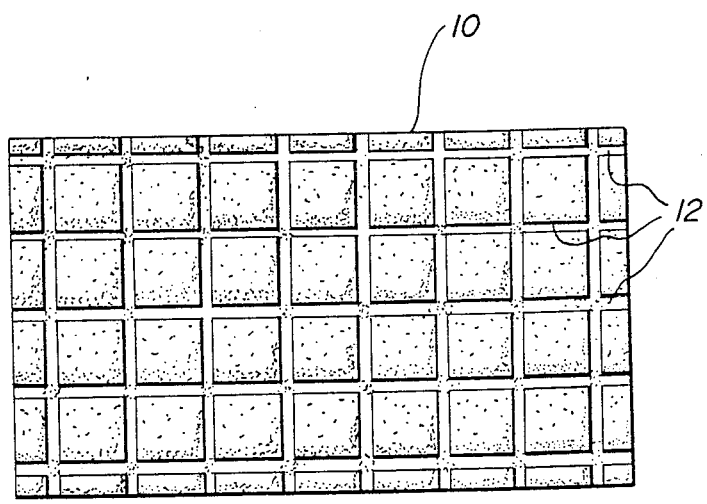
FIG. 2 is a top view of the membrane of the present invention having an alternative pattern of ink-type material.

The moisture vapor permeable material of the present invention as observed in FIGS. 1 and 2, comprises a polyurethane backing member coated with an ink-type material. The ink-type material 12 is preferably placed on portions of the polyurethane membrane 10 as in the striped configuration observed in FIG. 1. The ink can be printed in any pattern and can be placed on the top or bottom of the membrane 10. Optimally, the ink-type material covers 1 to 85% of the surface area. The pattern indicated in FIG. 1 allows for greater stability and facilitates the removal of the "wing-type" release liner and subsequent application of the product. This and other ink patterns can reinforce the polyurethane membrane enough to eliminate the need for a frame on the product, as is necessary in prior art membranes. Another configuration of ink-type material on the backing member is observed in FIG. 2.

A number of different ink-type coatings have been used successfully to reinforce the polyurethane backing and still maintain sufficient moisture vapor transmission. Ideally, non-toxic inks along with medically approved colorants can be used. One such coating could be a co-solvent polyamide polymer system ink along with copper-phthalocyanine, a federally approved colorant. Another desirable ink material is styrene dissolved in a carrier such as alcohol or methyl ethyl ketone. It is also possible to employ polyethylene as the ink-type material.

The ink-type material can be applied to the polyurethane membrane in any suitable fashion currently known in the art. For instance, the ink can be applied by conventional printing machines and methods. One such method suitable for depositing the ink on the membrane is known as the gravure flex method of printing. Additionally, the pattern of ink can be placed on the polyurethane by applying it in strips of either hot melt material, or of narrow tape. In all of these ways, a pattern of ink-type material can be placed on the polyurethane, resulting in a strengthened, effective product.

When used with a suitable adhesive, the ink-reinforced membranes of the present invention can be used to retain IV needles and the like in place on the skin of a patient. Such adhesive membranes are constructed by placing a suitable adhesive on the underside of the ink-coated polyurethane backing member by any conventional method. The adhesive used should be porous to allow transmission of moisture through the product or can be of the hydrophilic type such as those used with electrodes. The adhesive can be applied continuously or non-continuously across the backing member, forming any desired pattern which allows for sufficient adhesion to the skin. The resulting product is a strengthened moisture vapor-permeable adhesive suitable for use in retaining IV needles, electrodes, or other devices on the skin of the patient.

The ink-reinforcement process of the present invention is not limited to moisture vapor permeable materials, but can also be used on other thin films which are not moisture vapor-permeable. Ink reinforcement can be applied to a number of moisture vapor-impermeable thin films, such as Saran Wrap, in order to impart further strength, body and tear-resistance to these materials as well. As with the polyurethane membranes, the ink-type materials can be applied in any suitable fashion presently known in the art.

We claim:

1. A method of reinforcing a moisture-vapor-permeable polyurethane membrane comprising applying a coat of an ink material in a uniform pattern on the polyurethane membrane to strengthen the membrane.

2. A method of reinforcing a polyurethane membrane as claimed in claim 1 wherein said ink material is applied in strips.

3. A method of reinforcing a moisture vapor-permeable polyurethane adhesive comprising applying a coat of an ink material on the polyurethane adhesive.

4. A method of reinforcing a polyurethane adhesive as claimed in claim 3 wherein said ink material is applied in strips.

5. A film material for use in medical applications comprising a continuous moisture vapor permeable member having at least a partial coating of ink developed in a uniform pattern on at least one surface of said moisture 6. A film material as claimed in claim 5 wherein said ink comprises a non-toxic ink with a medically approved colorant.

7. A film material as claimed in claim 6 wherein said non-toxic ink comprises a polyurethane polymer.

8. A film material as claimed in claim 5 wherein said colorant comprises a copper-phthalocyanin colorant.

9. A film material as claimed in claim 5 wherein said ink comprises polyethylene.

10. A film material as claimed in claim 5 wherein said ink is styrene dissolved in a carrier.

11. A film material as claimed in claim 10 wherein the carrier comprises methyl ethyl ketone.

12. A film material as claimed in claim 10 wherein the carrier comprises alcohol.

13. A film material according to claim 5 and further including an adhesive coated on said moisture vapor permeable member.

* * * * *